(12) United States Patent
Yoda

(10) Patent No.: US 8,920,321 B2
(45) Date of Patent: Dec. 30, 2014

(54) PHOTOACOUSTIC IMAGING APPARATUS

(75) Inventor: Haruo Yoda, Nishitama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 460 days.

(21) Appl. No.: 12/999,302

(22) PCT Filed: Jun. 11, 2009

(86) PCT No.: PCT/JP2009/061059
§ 371 (c)(1), (2), (4) Date: Dec. 15, 2010

(87) PCT Pub. No.: WO2009/154244
PCT Pub. Date: Dec. 23, 2009

(65) Prior Publication Data
US 2011/0098550 A1   Apr. 28, 2011

(30) Foreign Application Priority Data

Jun. 18, 2008  (JP) ................... 2008-159313
Feb. 12, 2009  (JP) ................... 2009-029953

(51) Int. Cl.
| | |
|---|---|
| *A61B 8/00* | (2006.01) |
| *G01N 29/24* | (2006.01) |
| *A61B 5/00* | (2006.01) |
| *G01N 21/17* | (2006.01) |
| *G01S 7/52* | (2006.01) |
| *A61B 8/08* | (2006.01) |

(52) U.S. Cl.
CPC ............. *A61B 8/08* (2013.01); *G01N 29/2418* (2013.01); *A61B 5/0095* (2013.01); *G01N 21/1702* (2013.01); *G01S 7/52085* (2013.01); *A61B 8/4483* (2013.01); *A61B 5/0059* (2013.01)
USPC .......................................... 600/437

(58) Field of Classification Search
USPC ......................................... 600/437
See application file for complete search history.

(56) References Cited

U.S. PATENT DOCUMENTS

| | | | |
|---|---|---|---|
| 5,713,356 | A | 2/1998 | Kruger |
| 6,292,682 | B1 | 9/2001 | Kruger |

(Continued)

FOREIGN PATENT DOCUMENTS

| | | | |
|---|---|---|---|
| CN | 1518953 A | 8/2004 | |
| CN | 1575770 A | 2/2005 | |

(Continued)

OTHER PUBLICATIONS

Xing, et al., "Photoacoustic Imaging Technique of Tissue and Its Applications in Biomedicine", Optics Journal, Aug. 2007, pp. 26-33, vol. 44, No. 8.

(Continued)

*Primary Examiner* — Unsu Jung
*Assistant Examiner* — Saurel J Selkin
(74) *Attorney, Agent, or Firm* — Canon USA Inc. IP Division

(57) ABSTRACT

A bioinformation acquisition apparatus to input a signal having uniform sensitivity and a high SN ratio at a high speed is provided. It includes a moving device moving an element group into the arrangement direction of the elements, and moves the element group situated at a first position at first time point to be situated at a second position at second time point. The element group receives an elastic wave emitted from a test object at the first time point at the first position, and the elastic wave from the test object at the second time point at the second position. The electric signal of a specified position of a test body from a first element of the elastic waves received at the first time point and the electric signal of the specified position from a second element received at the second time point are added to each other.

15 Claims, 15 Drawing Sheets

(56) References Cited

U.S. PATENT DOCUMENTS

| 6,490,470 B1 | 12/2002 | Kruger |
| 2002/0193678 A1 | 12/2002 | Kruger |
| 2005/0004458 A1 | 1/2005 | Kanayama et al. |

FOREIGN PATENT DOCUMENTS

| JP | 60006860 A | 1/1985 |
| JP | 63058116 A | 3/1988 |
| JP | 2001-507952 T | 6/2001 |
| JP | 2003070786 A | 3/2003 |
| JP | 2005-021380 A | 1/2005 |
| JP | 2005291828 A | 10/2005 |
| WO | 9814118 A1 | 4/1998 |

OTHER PUBLICATIONS

Xiang, et al., "Noinvasive Photoacoustic Tomography in Biological Tissue with Ultrasonic Probe Beam", ACTA Photonica Sinica, Jul. 2007, pp. 1307-1311, vol. 36, No. 7.

The International Preliminary Report on Patentability (Chapter I) issued in international application No. PCT/JP2009/061059. 6 pages enclosed, Report dated Aug. 9, 2009.

PHOTOACOUSTIC IMAGING APPARATUS

TECHNICAL FIELD

The present invention relates to a bioinformation acquisition apparatus to image an elastic wave emitted from a test body.

BACKGROUND ART

A photoacoustic imaging method, which is a bioinformation acquisition method, is a method of detecting an acoustical wave induced in the internal portion of a living body by radiating a pulsed laser light to the living body, thereby imaging the three-dimensional structure of the internal portion of the living body. The acoustical wave is generated by the radiation of the pulsed laser light to a test object in a living body to cause the thermal expansion of the test object in the internal portion of the living body. Moreover, by changing the wavelength of the wavelength of the pulsed laser light, it is possible to visualize the distributions of specific substances, such as hemoglobin and glucose in blood, having an absorption band of the wavelength. Consequently, because a potential tumor, such as the abnormal growth of new blood vessels, can be non-invasively determined, the photoacoustic imaging method has been seen as a potential device for screening for breast cancer or the early detection thereof in recent years.

A conventional concrete procedure of the photoacoustic imaging method is disclosed in, for example, Published Japanese Translation of a PCT Application No. 2001-507952 as follows.

(1) Two-dimensionally arranged electromechanical conversion elements (transducers) are located on the surface of a test body, and single pulse electromagnetic energy is radiated to the test body.

(2) Just after the radiation of the electromagnetic energy, the signal received by each electromechanical conversion element is sampled to be stored.

(3) As to a point r' in the test body to be visualized, the delay time necessary for an acoustical wave to reach the position r of each electromechanical conversion element i from the point r' is calculated, and the signal of each electromechanical conversion element i corresponding to the calculated delay time is added to one another to be set as the image value at the point r'.

(4) The step (3) is repeated to each point r' to be imaged.

Moreover, Japanese Patent Application Laid-Open No. 2005-021380 discloses the method of reconstructing both of a photoacoustic image and an ordinary ultrasound echo image by using common one-dimensionally arranged electromechanical conversion elements, and the configuration of arranging an illumination system using glass fibers between the one-dimensionally arranged electromechanical conversion elements. Since the method disclosed in this Japanese Patent Application Laid-Open No. 2005-021380 uses the one-dimensionally arranged electromechanical conversion elements, the method is required to repeat the reconstruction by mechanically moving the one-dimensionally arranged electromechanical conversion elements into the direction perpendicular to the arrangement direction of the transducers in order to reconstruct a three-dimensional image.

In order to reconstruct the three-dimensional image by using the photoacoustic imaging method, it is desirable to use two-dimensionally arranged electromechanical conversion elements in order to reduce the direction dependency of an image resolution. As the methods for obtaining a photoacoustic image in a wide area on the premise of the use of the two-dimensionally arranged electromechanical conversion elements, the following methods can be considered: (1) the method of arranging electromechanical conversion elements on the whole wide area, and (2) the method of locating a comparatively small-scale electromechanical conversion element group (a group composed of arranged electromechanical conversion elements) in a step and repeat system to perform mechanical scanning. However, the method (1) has the problem of the difficulty of commercial viability in cost owing to the scale enlargement of the receiving system of the method. Moreover, the method (2) has the problem of the occurrence of the unevenness of sensitivity between the central part and the end parts of the two-dimensionally arranged electromechanical conversion elements. Moreover, the method (2) has the problem of the waste of time to locate the electromechanical conversion element group to the next positions one by one in the step and repeat system.

DISCLOSURE OF THE INVENTION

Accordingly the present invention is directed to provide a bioinformation acquisition apparatus capable of performing the mechanically scanning using an electromechanical conversion element group to receive elastic waves in a wide inspection area, and capable of inputting a signal having uniform sensitivity and a high SN ratio at a high speed.

An aspect of the present invention is a bioinformation acquisition apparatus, comprising: an electromechanical conversion element group including a plurality of arranged electromechanical conversion elements, each receiving an elastic wave emitted from a test object in a test body to convert the received elastic wave into an electric signal; a moving device moving the electromechanical conversion element group into an arrangement direction of the electromechanical conversion elements; an adding device adding electric signals transmitted from the plurality of electromechanical conversion elements; and a processing device reconstructing an image of an inner part of the test body based on an added signal added by the adding device; wherein the moving device moves the electromechanical conversion element group so that the electromechanical conversion element group situated at a first position at a first time point may be situated at a second position at a second time point, the electromechanical conversion element group receives elastic waves emitted from the test object at the first time point at the first position, and receives the elastic waves emitted from the test object at the second time point at the second position, and the adding device adds an electric signal transmitted from a first electromechanical conversion element corresponding to a specified position of the test body among electric signals of the elastic waves received at the first time point and an electric signal transmitted from a second electromechanical conversion element corresponding to the specified position among electric signals of the elastic waves received at the second time point.

According to the aspect of the present invention, the elastic waves in a wide inspection area are received by the mechanically scanning using the electromechanical conversion element group, and consequently the signals having uniform sensitivity and high SN ratios can be input at a high speed.

Further features of the present invention will become apparent from the following description of exemplary embodiments with reference to the attached drawings.

BEST MODE FOR CARRYING OUT THE INVENTION

The elastic waves in the present invention include the waves called as an acoustic wave, an ultrasound, an acoustical wave, and a photoacoustic wave, and include, for example, an acoustical wave generated in the inner part of a test body when a light, which is an electromagnetic wave, such as a near infrared ray, is radiated to the inner part of the test body. Moreover, the elastic waves emitted from a test body include an elastic wave generated at some portion or at a certain portion of the test body. That is, a bioinformation acquisition apparatus of the present invention includes a photoacoustic imaging apparatus, which radiates a light, being an electromagnetic wave, to the inner part of a test body and receives an acoustical wave generated in the inner part of the test body with a probe to display a tissue image of the inner part of the test body.

A laser can be used as an electromagnetic wave source in the present invention, and even electromagnetic waves emitted from a light emitting diode, a xenon lamp, and the like can be generally used in the present invention besides the laser light.

First Embodiment

In the following, a first embodiment of the present invention will be described. A bioinformation acquisition apparatus according to the present embodiment includes a light source, as an electromagnetic wave source for generating a pulsed laser; and an electromechanical conversion element group, which includes a plurality of arranged electromechanical conversion elements, each receiving an acoustical wave, as an elastic wave generated by radiating a pulsed laser from the light source to a test object in a test body, and converting the received acoustical wave into an electric signal. Furthermore, the bioinformation acquisition apparatus includes a moving device for moving the electromechanical conversion element group into the arrangement direction of the electromechanical conversion elements, an adding device for adding the electric signals transmitted from the plurality of electromechanical conversion elements to one another, and a processing device for obtaining image information on the basis of the added signal added by the adding device.

Figure 1:
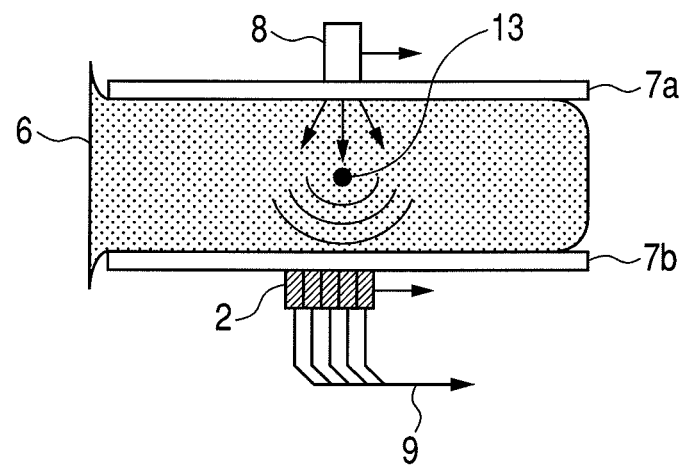
FIG. 1 is a view illustrating the principle of a bioinformation acquisition apparatus according to a first embodiment.

In the following, the embodiments of the present invention will be described with reference to the attached drawings. FIG. 1 is a view illustrating the principle of receiving an acoustic signal. In FIG. 1, a test body 6 is fixed so as to be nipped by press plates 7a and 7b from both the upper and lower sides thereof. A pulsed laser light is radiated from a light source 8 as an electromagnetic wave source, which is situated on the press plate 7a, for generating a pulsed laser to the test body 6. As a result, hemoglobin and the like in the test object in the inner part of the test body 6 absorbs the energy of the laser light, and the temperature of the test object rises according to the absorbed energy quantity. The test object instantaneously swells due to the rise of the temperature to generate an acoustical wave. The generated acoustical wave is converted into an electric signal 9 by an electromechanical conversion element group 2 arranged to be in contact with the lower side press plate 7b, and the converted electric signal 9 is output to the subsequent stage. Incidentally, the light source 8 may be the emission of a light led from a light source situated at a distant position with a mirror or a glass fiber. Moreover, the light source 8 may be provided integrally with the bioinformation acquisition apparatus of the present invention, or may be provided as separated from the bioinformation acquisition apparatus.

The light source 8 is desirably a pulsed laser light source capable of generating a pulsed laser light in the order of several nanoseconds to several hundred nanoseconds in order to efficiently generate an acoustical wave from the test object. In this case, the wavelength of the pulsed laser light can be within a range of from 400 nm to 1600 nm, both inclusive. Furthermore, the wavelength can be more preferably within a region of from 700 nm to 1100 nm, in which the absorption of the laser light in the living body is little. Various lasers, such as a solid state laser, a gas laser, a dye laser, and a semiconductor laser, can be used as the laser.

Figure 2:
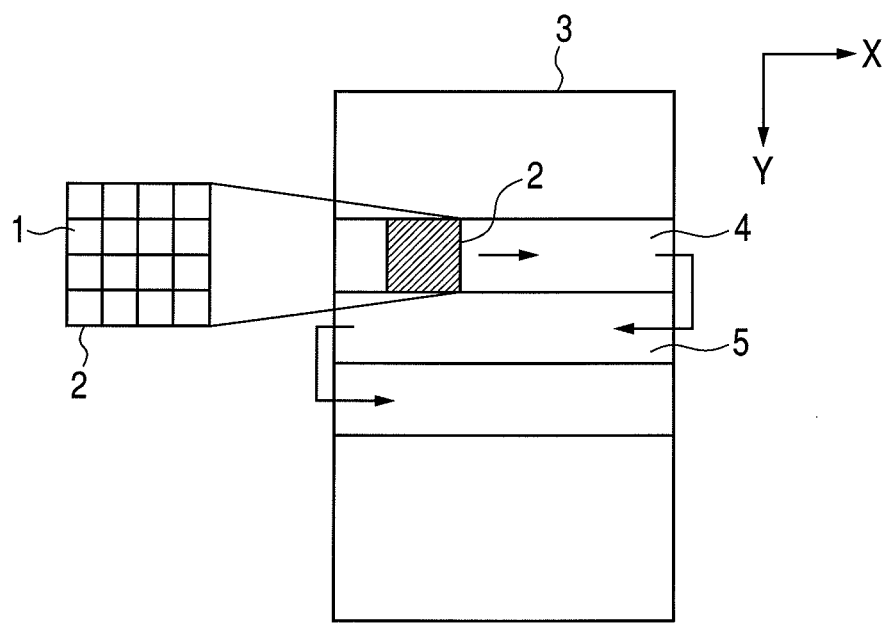
FIG. 2 is a view illustrating a method for inputting an acoustical wave of a wide area according to the first embodiment.

Next, the method of inputting an acoustic signal in a wide area 3 in conformity with the receiving principle will be described with reference to FIG. 2. In FIG. 2, the electromechanical conversion element group 2 is an arrangement of a plurality of electromechanical conversion elements 1 in a two-dimensional grating. At the time of receiving the acoustical wave in the wide inspection area 3, as illustrated in FIG. 2, the electromechanical conversion element group 2 is moved in a direction (X direction) to complete the reception of the acoustical waves in a stripe region 4, and then the electromechanical conversion element group 2 is moved in a direction (Y direction) perpendicular to the first moving direction to be located. Then, the electromechanical conversion element group 2 is moved again to perform the reception in the adjoining stripe region 5, and thus the reception of the acoustical waves can be executed by repeating the procedure mentioned above. As described above, the movement of the electromechanical conversion element group 2 into the arrangement direction of the electromechanical conversion elements 1 in the present invention means to move the electromechanical conversion elements 1 into the X direction or the Y direction in the case where the electromechanical conversion elements 1 are arranged in a two-dimensional grating.

Moreover, the electromechanical conversion elements 1 of the present embodiment are required to detect the acoustical wave to be generated from a test object 13 in the test body 6 that has absorbed a part of the energy of the light radiated from the light source 8 to the test body 6 to convert the detected acoustical wave into the electric signal 9. Accordingly, it is desirable to optimize the frequency band that the electromechanical conversion elements 1 can receive according to the size of the test object 13 in the test body 6.

Any detector, such as a transducer using a piezoelectric effect, a transducer using the resonance of light, and a transducer using a change of a capacity, as long as the detector can detect an acoustical wave, may be used as the electromechanical conversion elements 1. For example, if the acoustical waves generated from variously sized test objects are received, then a transducer using the changes of capacities of a wide detection frequency band or a plurality of transducers having different detection bands can be used.

Figure 3:
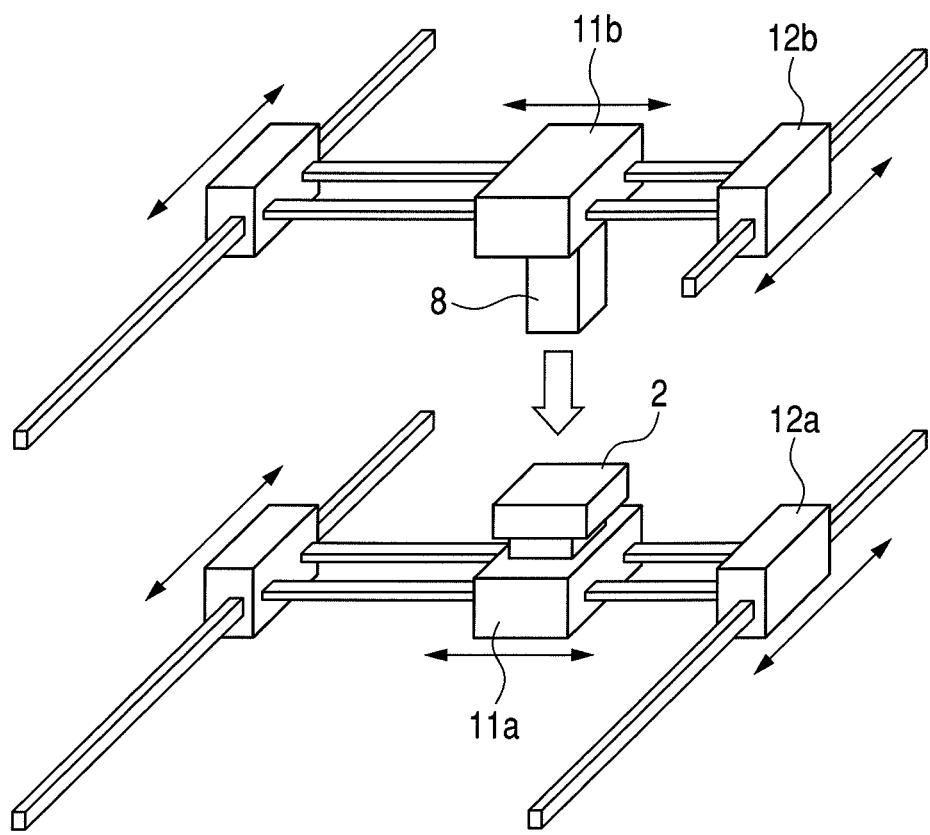
FIG. 3 is a view illustrating an X-Y moving mechanism for mechanical scanning according to the first embodiment.

FIG. 3 illustrates an X-Y moving mechanism for the mechanical scanning of the electromechanical conversion element group 2 and the light source 8 along the test body 6. As illustrated in FIG. 3, the movements of the present embodiment can be easily realized by the combination of X direction moving mechanisms 11a and 11b and Y direction moving mechanisms 12a and 12b, which perform the step and repeat movements of the X direction moving mechanisms 11a and 11b into the Y direction. The light source 8 may be moved independent of the electromechanical conversion element group 2, but the light source 8 is preferably moved integrally with the electromechanical conversion element group 2 since the range that the light source 8 can illuminate is generally limited.

Figure 4:
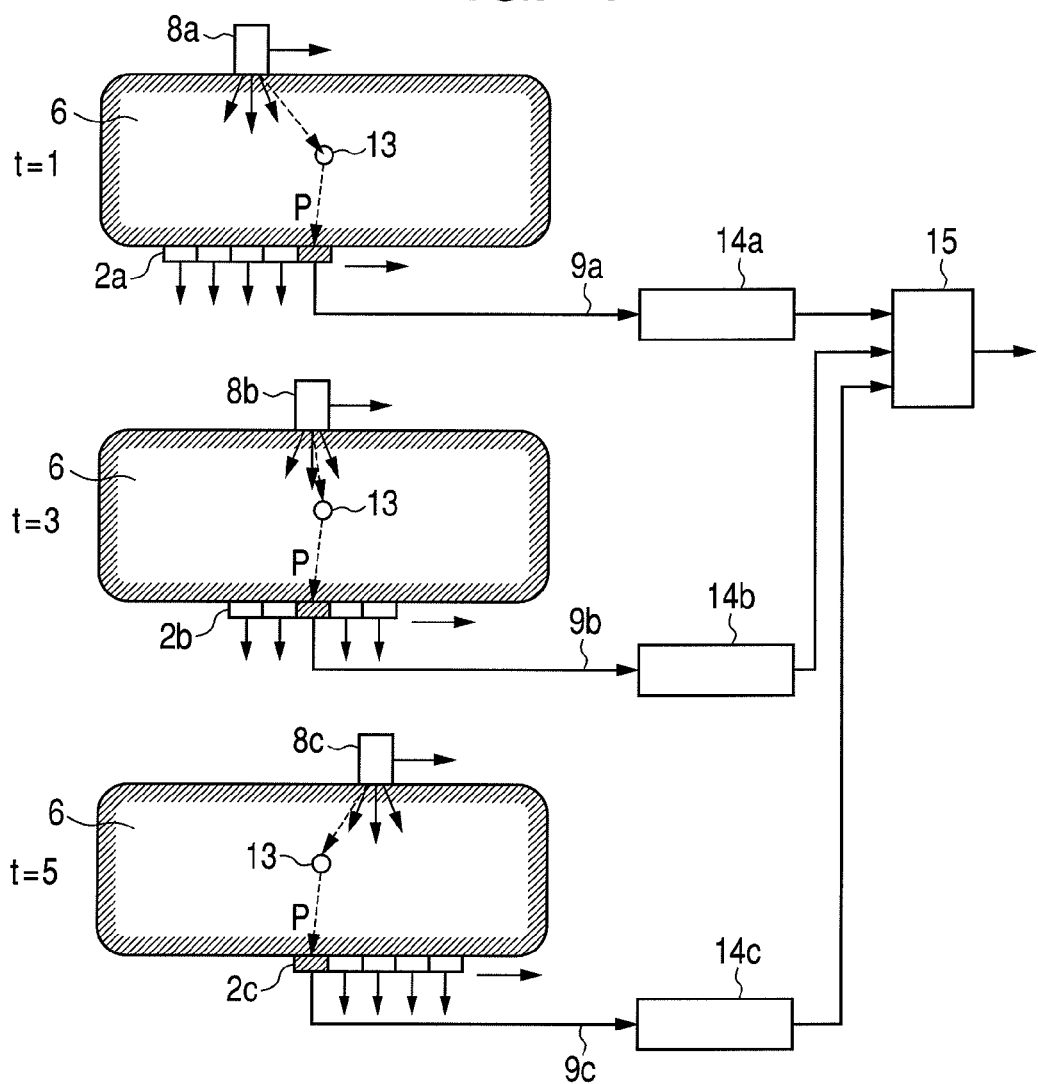
FIG. 4 is a view illustrating the operation principle of the bioinformation acquisition apparatus according to the first embodiment (in the case of moving a light source and an electromechanical conversion element group integrally).

FIG. 4 is a view illustrating the operation principle in the case where the light source 8 and the electromechanical conversion element group 2 are integrally moved into arrow directions. In FIG. 4, hemoglobin and the like in blood, which are to be detected, exist in the test object 13, and the light source 8 and the electromechanical conversion element group 2 are situated as light sources 8a, 8b, and 8c and the electromechanical conversion element groups 2a, 2b, and 2c at respective time points ($t=1$, $t=3$, and $t=5$) (the cases of $t=2$ and $t=4$ are omitted for simplification).

At the time of $t=1$, the test object 13 irradiated by the light source 8a generates an acoustical wave, and the acoustical wave reaching the position of a point P, which is a specified position in the test body 6, is converted into an electric signal 9a by a first electromechanical conversion element to be stored in a temporary storage memory 14a.

At the time of $t=3$, the acoustical wave of the test object 13 irradiated by the light source 8b is converted into an electric signal 9b at the point P, which is the same specified position in the test body 6 as the point P at the time of $t=1$, by a third electromechanical conversion element to be stored in a temporary storage memory 14b.

Similarly, at the time point of $t=5$, the acoustical wave is converted into an electric signal 9c at the point P, the specified position, by a fifth electromechanical conversion element to be stored in a temporary storage memory 14c. At this time, the severally stored electric signals 9 are signals for a certain period after the laser radiation, and are stored by being converted into one-dimensional digital waveform signal by an AD converter (not illustrated).

In the present embodiment, the moving device moves the electromechanical conversion element group 2 so that the electromechanical conversion element group 2 may be situated as the electromechanical conversion element groups 2a, 2b, and 2c at the time of the time points $t=1$, $t=3$, and $t=5$, respectively.

That is, the moving device moves the electromechanical conversion element group 2 so that the acoustical wave at the point P, the specified position in the test body 6, may be received by the first, third, and fifth electromechanical conversion elements at the time of the time points $t=1$, $t=3$, and $t=5$, respectively.

In the present embodiment, the moving device typically moves the electromechanical conversion element group 2 so that the acoustical waves reaching the specified position in the test body 6 at the predetermined time points can be received by the different electromechanical conversion elements. By moving the electromechanical conversion element group 2 in this way, the moving device can add the electric signals 9 to one another, which have been caused by the acoustical waves and reach the specified position in the test body 6 at the predetermined time points.

The movement of the electromechanical conversion element group 2 by the moving device of the present embodiment is based on the following consideration. That is, there is the problem that the receiving position of an acoustical wave moves during the reception of the acoustical wave because the electromechanical conversion element group 2 is being continuously moved while the acoustical wave is received. However, the reception time of the acoustical wave is as an extremely short time here as in the extent of 50 μs to 100 μs at the most after the radiation of a pulsed laser light. On the other hand, the period of the radiation of the pulsed laser light is generally limited to a slow period in the extent of 100 ms in order to avoid damaging the living body. Accordingly, the electromechanical conversion elements should be moved at a low speed in accordance with the slow radiation period, and consequently almost no differences in effect are produced between the case of receiving the acoustical wave while moving continuously and the case of receiving the acoustical wave in the state of being stopping. That is, the time points of light radiation, acoustical wave generation, and acoustical wave reception can be regarded to be at the same time. By receiving the acoustical wave while being continuously moving in such a way, the moving time of the electromechanical conversion element group 2 and the time for locating the electromechanical conversion element group 2 can be omitted and high speed signal inputting can be performed.

Figure 5:
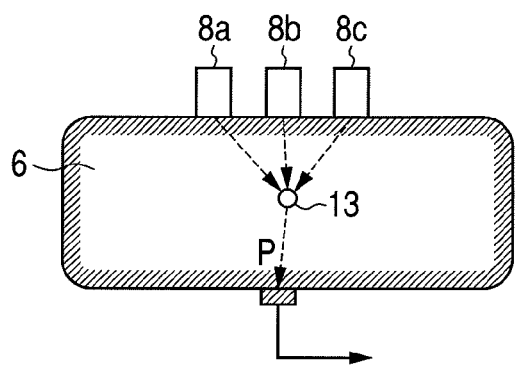
FIG. 5 is a view for describing an advantage of the invention implemented as the first embodiment.

The stored one-dimensional digital waveform signals are parallely read out at an appropriate time point, and are added to one another as a one-dimensional waveform signal by an addition circuit 15. By such a process, a plurality of times of acoustic signals reaching the same point P from the same test object 13 is added to one another, and the SN ratio of the received signal at the point P can be improved. Moreover, in view of the same point P on the test body 6 at this time, the added acoustic signals are the added acoustical wave signals illustrated at relatively different positions as illustrated in FIG. 5, and are equivalent to the acoustic signals emitted from the three light sources 8a, 8b, and 8c at the different positions at the same time. Consequently, the spatial illumination unevenness of the light sources 8a, 8b, and 8c is thereby smoothed, and the further improvement of the qualities of the received signals can be achieved. In particular, in the case of the system of the present embodiment, the smoothing of the illuminations like this is performed everywhere in a stripe, and consequently the illumination unevenness at the boundary part of the electromechanical conversion element group 2, which especially becomes a problem, can be decreased.

Incidentally, this feature can be realized by the movement into the arrangement direction in both of one-dimensionally arranged electromechanical conversion elements and two-dimensionally arranged electromechanical conversion elements. In the case of the two-dimensionally arranged electromechanical conversion elements, a speeding-up effect can be obtained by the parallel processing of a supposed plurality of one-dimensionally arranged electromechanical conversion elements.

Figure 6:
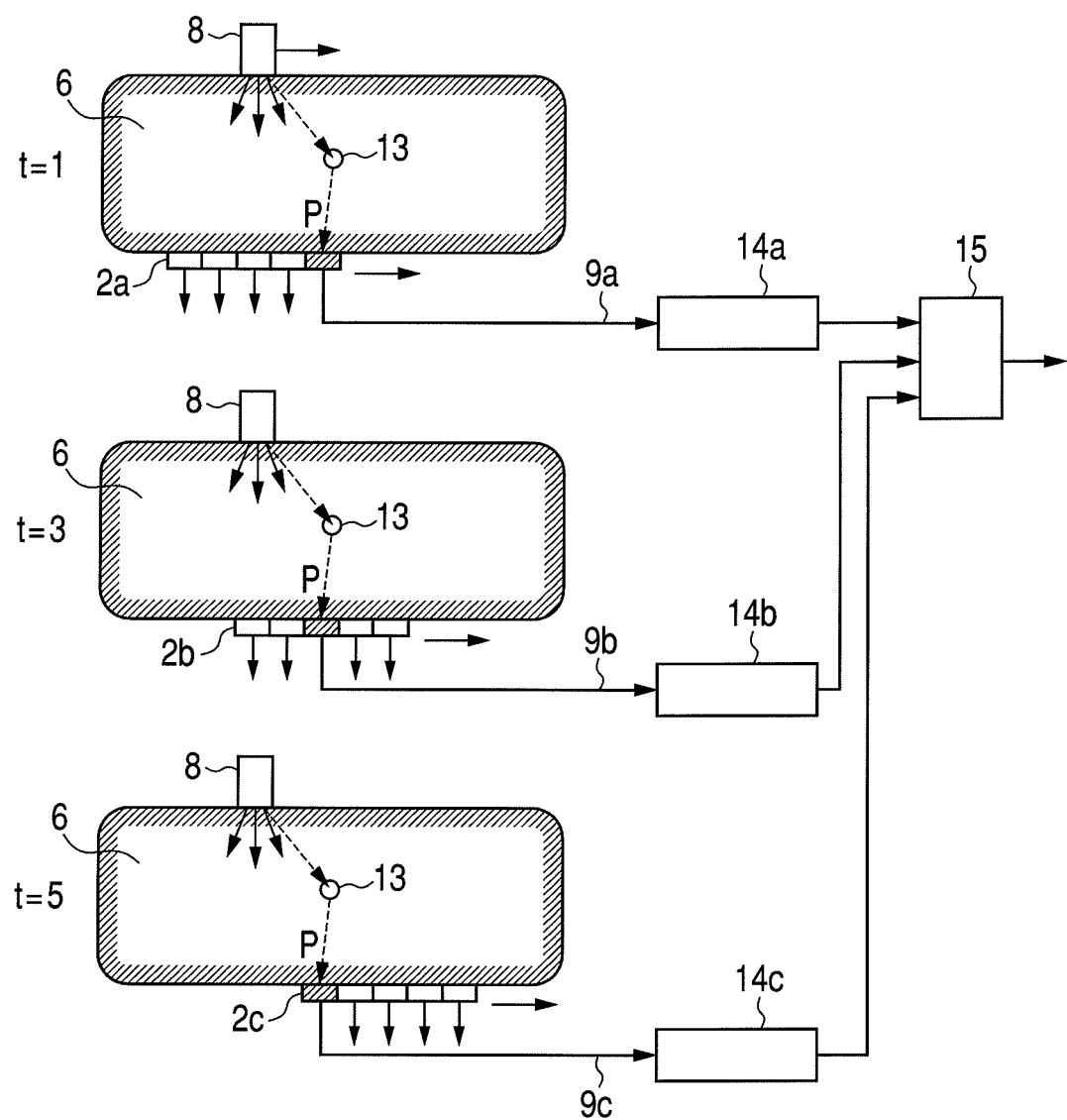
FIG. 6 is a view illustrating the operation principle of the bioinformation acquisition apparatus according to the first embodiment (in the case of fixing the light source and moving the electromechanical conversion element group).

Moreover, the example of the movement of the light source 8 as the light sources 8a to 8c as the changes of the time points from t=1 to t=5 is illustrated in FIG. 4, but the light source 8 may be left to be fixed at a specified position as illustrated in FIG. 6. However, since the range in which the pulsed laser lights from the light source 8 are radiated is limited, it is necessary for the light source 8 to be moved so that the pulsed laser lights may reach at least the test object 13. That is, the light source 8 is preferably moved so as to keep a certain relative position to the electromechanical conversion element group 2 in order that the pulsed laser lights may reach the test object 13.

Incidentally, the acoustic waves reaching the point P among the acoustic waves generated from the test object 13 have been described with reference to FIG. 4 in order to simplify the description. However, since the acoustical waves generated from the test object 13 actually propagate in each direction, the acoustical waves are detected at the positions other than the point P, the specified position.

The contents described above are summarized as follows.

The moving device moves the electromechanical conversion element group 2 so that the electromechanical conversion element group 2a situated at the first position at the first time point (e.g. t=1) may move as the electromechanical conversion element group 2b situated at the second position at the second time point (e.g. t=3).

The light source 8a radiates a pulsed laser to the test object 13 at the first time point (t=1), and the electromechanical conversion element group 2 receives the acoustical wave from the test object 13 as the electromechanical conversion element group 2a at the first position at the same first time point. Furthermore, the light source 8b radiates a pulsed laser to the test object 13 at the second time point (t=3), and the electromechanical conversion element group 2 receives the acoustical wave generated from the test object 13 as the electromechanical conversion element group 2b at the second position at the same second time point.

The addition circuit 15, which is the adding device, adds the following electric signals 9a and 9b to each other. That is, the electric signal 9a is an electric signal generated by the first electromechanical conversion element (first transducer) corresponding to the specified position (point P) in the test body 6 among the acoustical waves received at the first time point (t=1). The electric signal 9b is the electric signal generated by the second electromechanical conversion element (third transducer) corresponding to the specified position (point P) among the acoustical waves received at the second time point (t=3).

Figure 7:
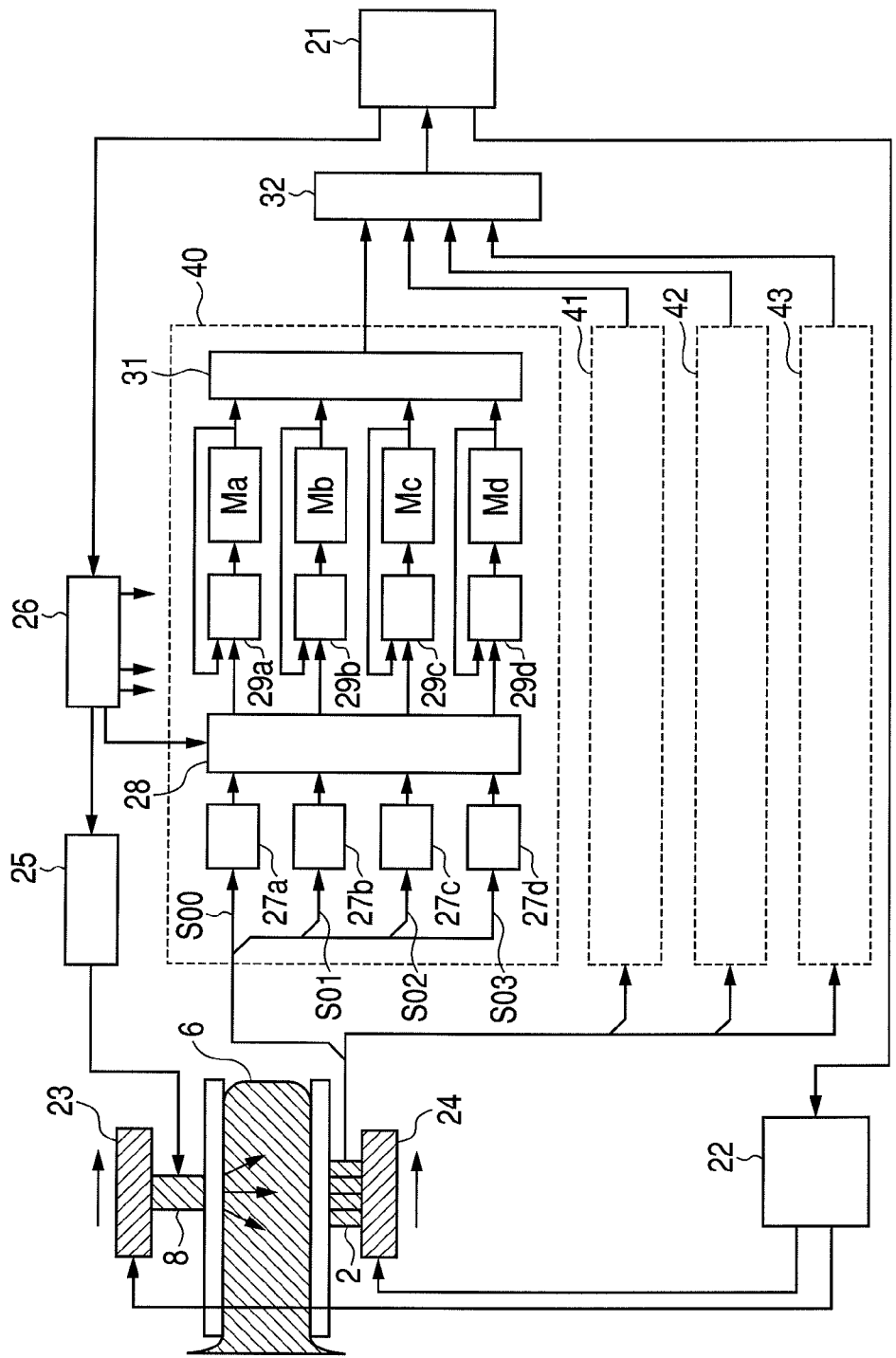
FIG. 7 is a view illustrating the concrete configuration of a received signal processing unit of the bioinformation acquisition apparatus according to the first embodiment.

Next, the concrete configuration of a received signal processing unit will be described with reference to FIG. 7. A processor 21 as a processing device for controlling the whole and performing image reconstruction from received signals is situated on the right end in FIG. 7, and a mechanical section for signal inputting, which includes the test body 6, is situated on the left end in FIG. 7. The light source 8 and the electromechanical conversion element group 2 are mounted on stages 23 and 24, respectively, and are moved by a stage control circuit 22. In this figure, the electromechanical conversion element group 2 uses a four-by-four element arrangement as a concrete example.

The light source 8 is controlled to emit a light by a laser control circuit 25 in synchronization with the position of the electromechanical conversion element group 2, and acoustical wave signals within a certain time after laser light emission are parallely input from the four-by-four reception elements. Signals S00, S01, S02, and S03 from the four elements (four elements situated at the most inner part in the normal line direction of the paper surface) arranged in the moving direction indicated by an arrow in FIG. 7 are converted into one-dimensional digital waveform signals by AD converters 27a, 27b, 27c, and 27d, respectively, in a circuit block 40. Then, the converted signals are subjected to accumulation additions into temporary storage memories Ma, Mb, Mc, and Md selected by the rotation shift circuit 28 as waveform signals by using adders 29a, 29b, 29c, and 29d, respectively. The one-dimensional digital waveform signals that have been subjected to predetermined times of accumulation additions in the temporary storage memories Ma, Mb, Mc, and Md are transferred to the processor 21 through selection circuits 31 and 32. The signals of the electromechanical conversion elements other than the four elements arranged in the moving direction are also parallely processed by similar circuit blocks 41, 42, and 43, and are transferred to the processor 21 by time-sharing. These series of procedures are controlled by a time point control circuit 26, which has received an instruction from the processor 21. The processor 21 reconstructs a three-dimensional image at a position corresponding to a received stripe on the basis of the transferred digital waveform signals.

Figure 8:
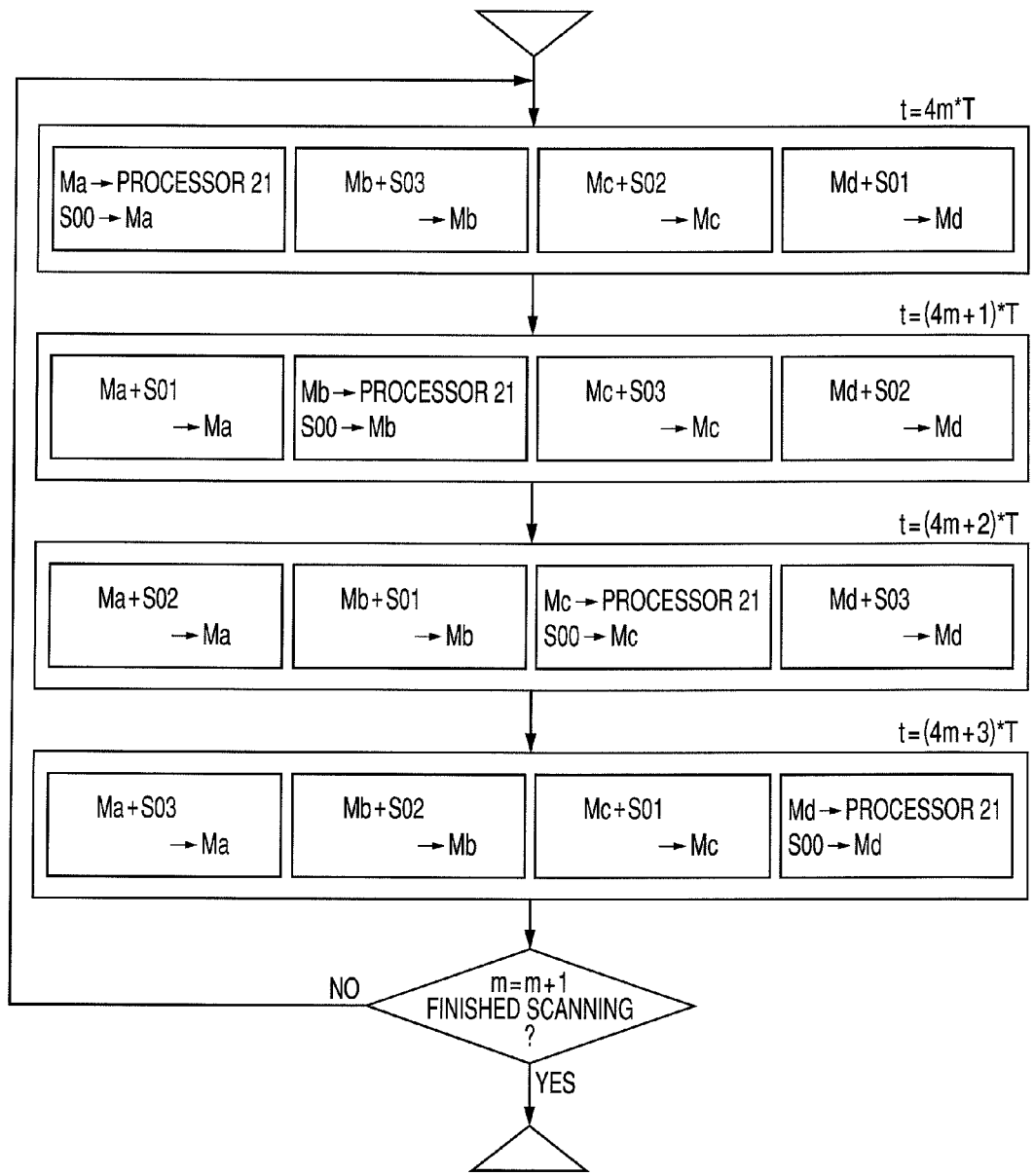
FIG. 8 is a diagram illustrating a flow chart of the accumulation addition processing of the bioinformation acquisition apparatus according to the first embodiment.

FIG. 8 illustrates the concrete operations of the rotation shift circuit 28 and accumulation addition circuits (each of the couple of the adder 29a and the memory Ma, the adder 29b and the memory Mb, the adder 29c and the memory Mc, and the adder 29d and the memory Md) in a flow chart format. In this flow chart, the processing corresponding to each of the temporary storage memories Ma, Mb, Mc, and Md is all parallely executed, the processing that is parallely executed is notated in each block side by side.

First, the processing corresponding to the temporary storage memory Ma will be described in order. Each block in the flow chart is processed one by one in each period T for receiving an acoustical wave. At a time point t=4m*T, the temporary storage memory Ma transfers the contents thereof to the processor 21, and inputs and stores the signal S00 as it is without performing the addition processing thereof. At a time point t=(4m+1)*T, the temporary storage memory Ma adds the signal S01 to the contents of the temporary storage memory Ma as a one-dimensional waveform and restores the added contents. At a time point t=(4m+2)*T, the temporary storage memory Ma adds the signal S02 to the contents of the temporary storage memory Ma as a one-dimensional waveform and restores the added contents. At a time point t=(4m+3)*T, the temporary storage memory Ma adds the signal S03 to the contents of the temporary storage memory Ma as a one-dimensional waveform and restore the added contents. After the completion of the processing at a time point t=(4m+3)*T, the temporary storage memory Ma increments the letter m to return its processing to that at the time point t=4m*T again. The addition result of the four transducer signals are stored in the temporary storage memory Ma every four periods by performing the processing described above, and the stored contents are transferred to the processor 21.

The processing similar to that of the temporary storage memory Ma is executed to the temporary storage memory Mb at the time point that shifts from that of the processing to the temporary storage memory Ma by the period T as illustrated in the flow chart of FIG. 8. The processing to the temporary storage memories Mc and Md are the same. That is, the signals input from a specific reception element are associated with the temporarily storage memories Ma, Mb, Mc, and Md every period T, which is a unit time, in the order of the temporarily storage memories Ma, Mb, Mc, Md, Ma, . . . . Since the temporarily storage memories Ma, Mb, Mc, and Ma of each signal do not overlap with one another at the same time points at this time, the assignment of received signals can be realized by the rotation shift circuit 28 as described above. Moreover, since the transfer time point to the processor 21 is also processed in order by each of the temporarily storage memories Ma, Mb, Mc, and Md, the transfer by time-sharing can be easily performed.

Figure 9:
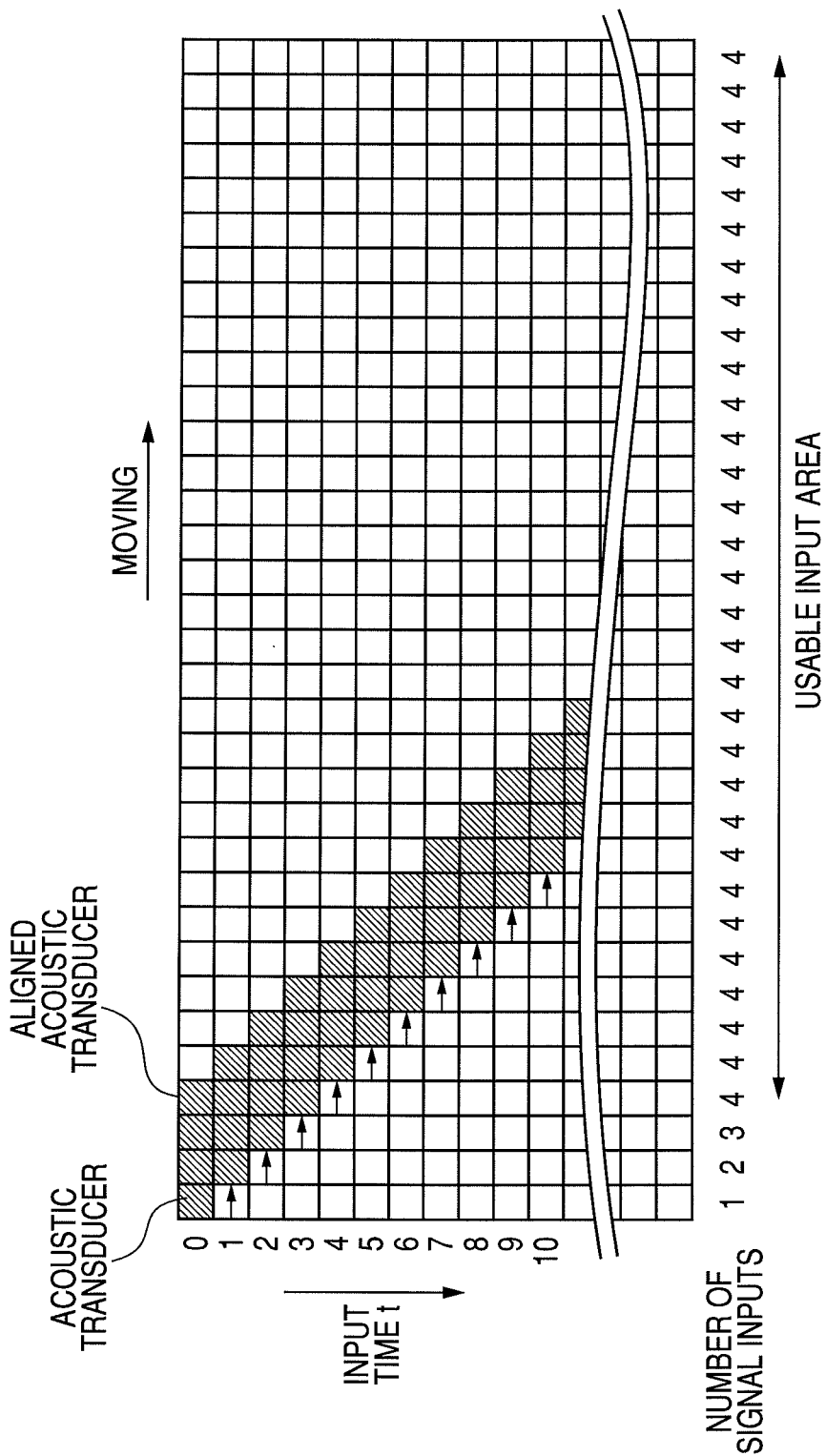
FIG. 9 is a diagram illustrating the time transitions of the accumulation additions in the bioinformation acquisition apparatus according to the first embodiment (at the time of movements by one-element width).

FIG. 9 illustrates the time transitions of accumulation additions by taking the positions of the moving direction on the abscissa axis and input times on the ordinate axis. In FIG. 9, four transducers are moved in their arrangement direction and the laser light source 8 emits a light to input an acoustic signal every movement of the width of an element.

If the acoustic signals are input in this way and the accumulation additions are performed to each position of the test body 6, as illustrated by the numerals at the lowermost step, signals can be added to one another four times to each area except for the first portion. Since about twofold improvement of SN ratios can be expected by the four times of signal additions, a three-dimensional image having an improved SN ratio can be produced by inputting the portion in which four times of additions are performed into the processor 21 as a usable input area to use the area for image reconstruction.

Figure 10:
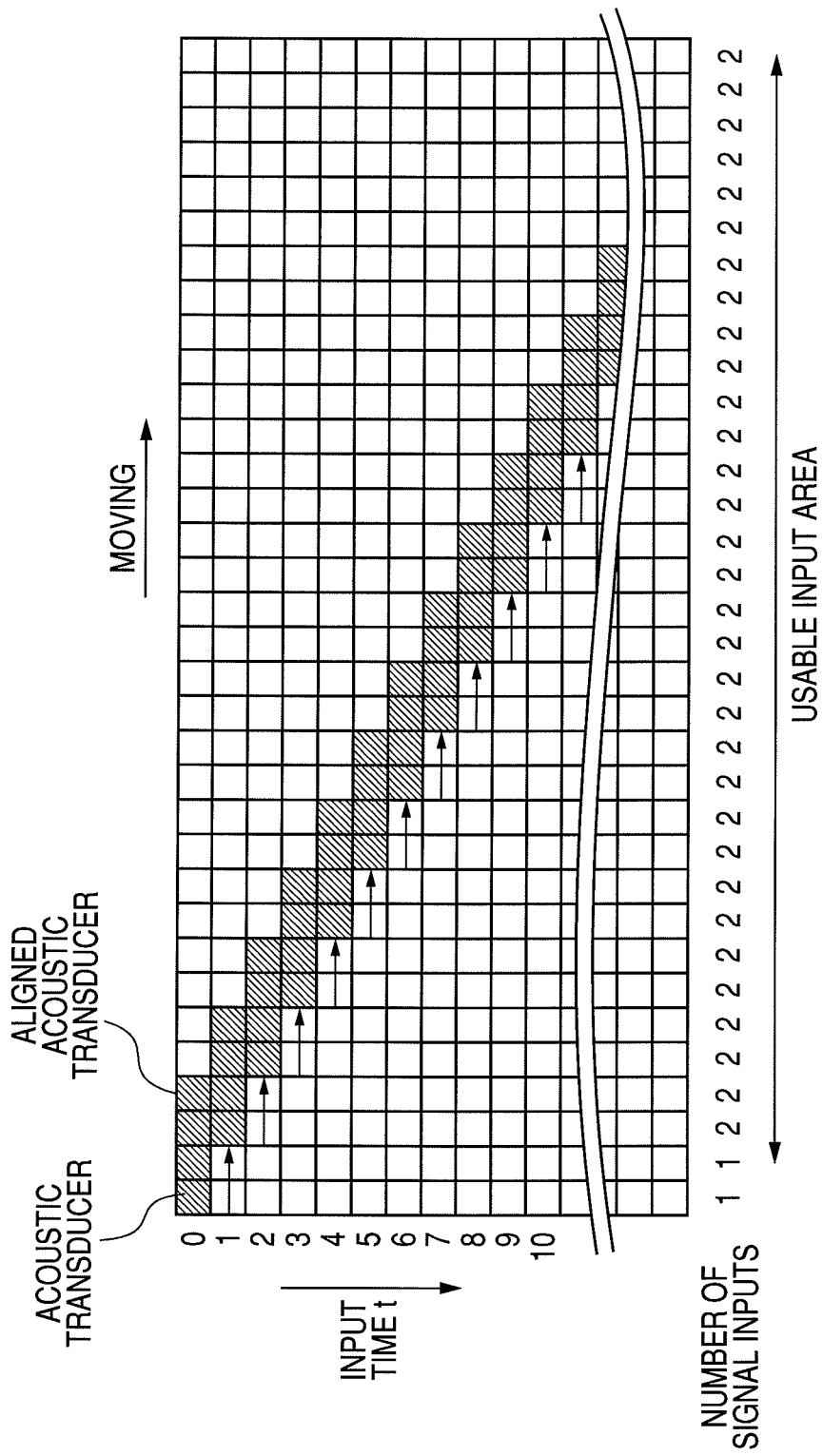
FIG. 10 is a diagram illustrating the time transitions of the accumulation additions in the bioinformation acquisition apparatus according to the first embodiment (at the time of movements by two-element width).

FIG. 10 is a diagram illustrating another example of the time transitions of accumulation additions. FIG. 10 illustrates the situation at the time of inputting an acoustic signal every movement of a two-element width. Since signals are added to each other two times in every area in this case, the improvement rate of the SN ratio is slightly smaller than that of the preceding example, but the stage speed of scanning a stripe is improved to be twice. Generally, if an acoustical signal is set to be input every movement of a d-element width, in which d is one of the measures of M, in the case of moving arrangement elements including M elements, then added signals of M/d times can be obtained, and the stripe scanning speed becomes faster in proportion to d. The maximum addition times is M times at the time of d=1, and the minimum addition times is one time at the time of d=M. Moreover, although the examples of FIGS. 9 and 10 have been described by using an electromechanical conversion element that is one-dimensionally arranged in the moving direction thereof, in the case of a two-dimensionally arranged element group including N arranged elements in the direction perpendicular to the moving direction of the element group, N sets of processing is parallely performed as described above.

According to the present embodiment of the present invention, signals having uniform sensitivity and high SN ratios can be input at high speeds in a bioinformation acquisition apparatus, which mechanically scans an electromechanical conversion element group to input an acoustic signal of a wide inspection area.

Second Embodiment

Next, a second embodiment of the present invention will be described. The second embodiment uses an electromechanical conversion element group different from that of the first embodiment. The other respects of the second embodiments are the same as those of the first embodiment.

Figure 11:
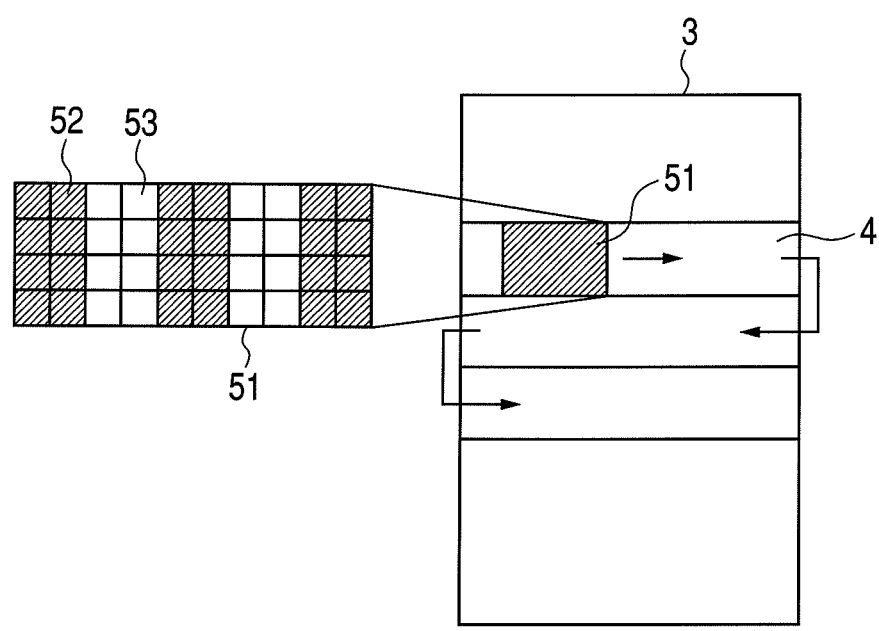
FIG. 11 is a view illustrating the scanning of an electromechanical conversion element group having gaps according to a second embodiment.
Figure 12:
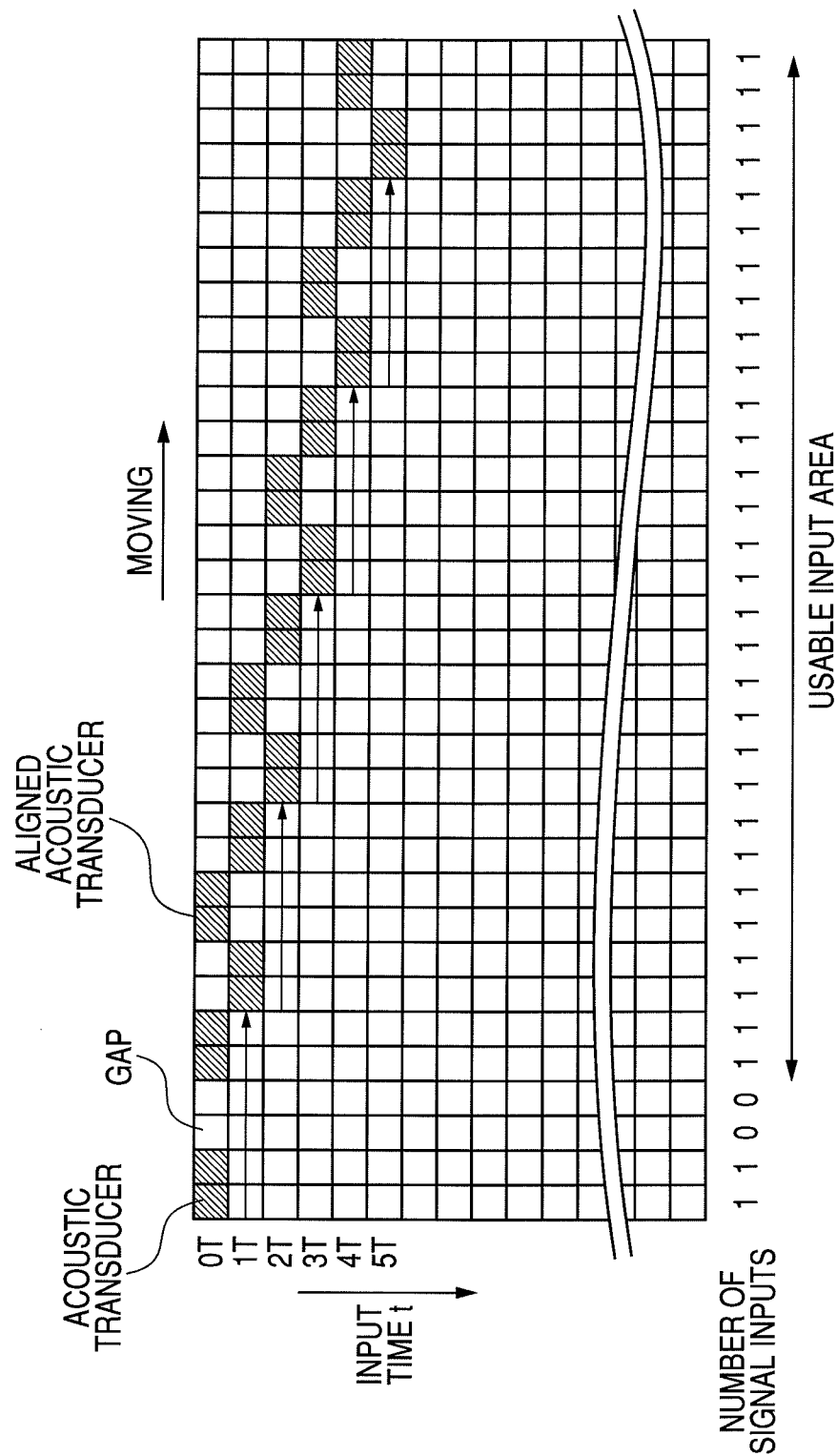
FIG. 12 is a diagram illustrating the time transitions of the accumulation additions in a bioinformation acquisition apparatus (having the gaps) according to the second embodiment (at the time of movements by six-element width).

As illustrated in FIG. 11, an electromechanical conversion element group 51 according to the present embodiment arranges six electromechanical conversion elements 52 in their moving directions with two gaps 53, each being a two-element width, put between the electromechanical conversion elements 52. FIG. 12 illustrates temporal transitions at the time of inputting an acoustic signal every movement of a six-element width by using the electromechanical conversion element group 51. As illustrated in FIG. 12, the inputting of the acoustic signals subjected to the addition of one time can be performed in successive positions in spite of using the electromechanical conversion element group 51 with the gaps 53 in this case. The electromechanical conversion element group 51 of the present embodiment is typically provided with the gaps 53 in the size of an integral multiple of the arrangement pitch of the electromechanical conversion elements 52.

Figure 13:
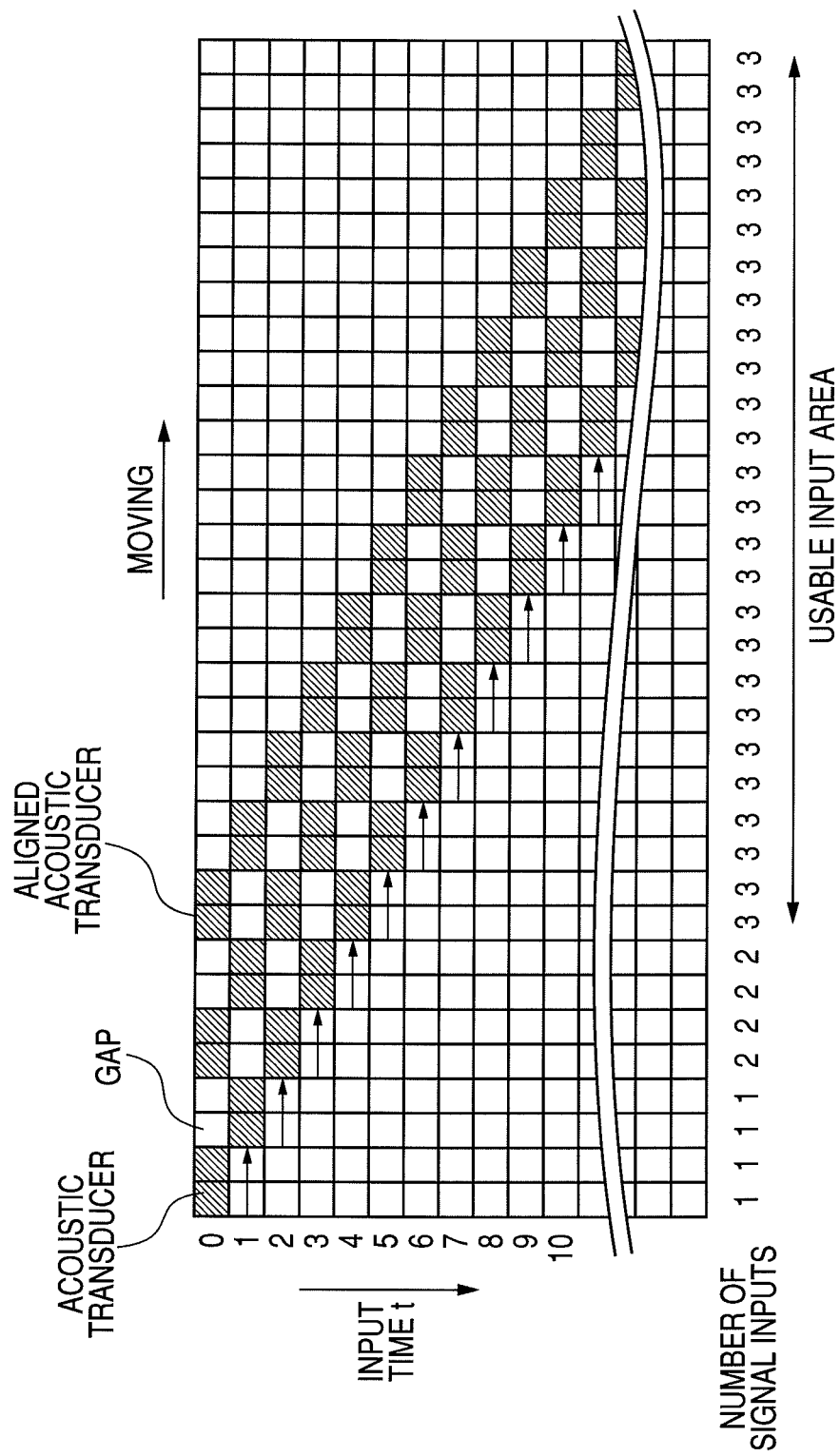
FIG. 13 is a diagram illustrating the time transitions of the accumulation additions in the bioinformation acquisition apparatus (having the gaps) according to the second embodiment (at the time of movements by two-element width).
Figure 14:
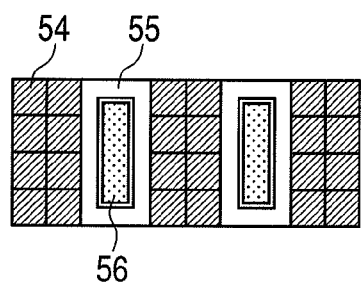
FIG. 14 is a view illustrating the electromechanical conversion element group according to the second embodiment, which has light sources arranged in the gap portions.

FIG. 13 illustrates the temporal transitions in the case of inputting an acoustic signal every movement of a two-element width by using the same electromechanical conversion element group 51 as that of FIG. 11. In this case, three times of acoustic signal additions can be performed. In this way, even if the gaps 53 exist in the electromechanical conversion element group 51, the same signal inputting as that of the electromechanical conversion element group having no gaps can be performed. Accordingly, for example, by arranging a light source unit 56 in a gap portion 55 between electromechanical conversion elements 54 as illustrated in FIG. 14, the illumination of a pulsed laser light from the side of the arranged electromechanical conversion elements 54 becomes easy. Since the attenuation of light intensity in a test body is large by the photoacoustic imaging method, the illumination of a pulsed laser light from the side of the arranged electromechanical conversion elements 54 is extremely effective for the improvement of the quality of a reconstructed image.

Figure 15:
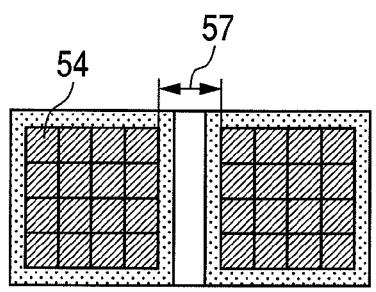
FIG. 15 is a view illustrating an electromechanical conversion element group according to the second embodiment, which uses a gap portion as a joining portion.

Furthermore, in the case of manufacturing an electromechanical conversion element group having a large number of elements, the method of forming the large electromechanical conversion element group by joining a plurality of small electromechanical conversion element groups, which can be easily manufactured, together is adopted. Also in this case, if the boundary parts 57 of small electromechanical conversion element groups are configured as the gap portion like the ones mentioned above as illustrated in FIG. 15, then the advantage that the sizes of the boundary parts 57 can be enlarged to make their manufacturing easy is obtained.

According to the present embodiment, as described above, various inputting methods can be performed by devising the arrangement of the electromechanical conversion elements and the time point of the inputting of acoustic signals. Generally, the repetition period of acoustic signal inputting is frequently limited to be a certain period or less in order to avoid damaging a test body. Accordingly, in the case where high speed inputting is necessary, the method of enlarging the movement speed to decrease the addition times is led to be selected, and in the case where high quality signal inputting is necessary, the method of reducing the movement speed to increase the addition times is led to be selected.

Third Embodiment

Next, a third embodiment of the present invention will be described. The third embodiment implements the addition processing in the direction perpendicular to the moving direction of an electromechanical conversion element group besides the addition processing in the moving direction of the electromechanical conversion element group. The other respects are the same as those of the first and second embodiments.

If acoustic signal inputting is performed by using an electromechanical conversion element group arranging M electromechanical conversion elements in the moving direction and N electromechanical conversion elements in the direction perpendicular to the moving direction, then the number of signal waveforms corresponding to the stripe length of the width of the N electromechanical conversion elements have been input into the processor 21 at the time point when a time of movement has been completed. Next, if an adjacent stripe is set so that a part of the adjacent stripe may overlap with the former stripe and an acoustical wave signal is taken into the processor 21 by a similarly continuous movement, then the addition of the data in the overlapping region can be performed on the processor 21.

Figure 16:
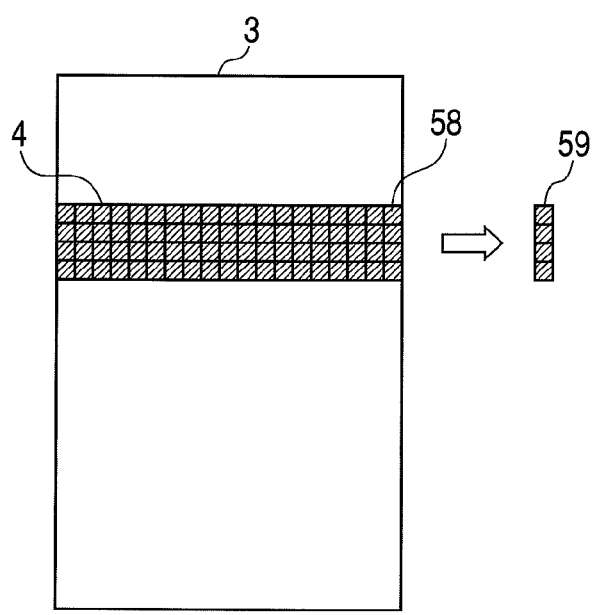
FIG. 16 is a view illustrating a method for expressing received signals arranged in two dimensions in a stripe as a one-dimensional arrangement according to a third embodiment.
Figure 17:
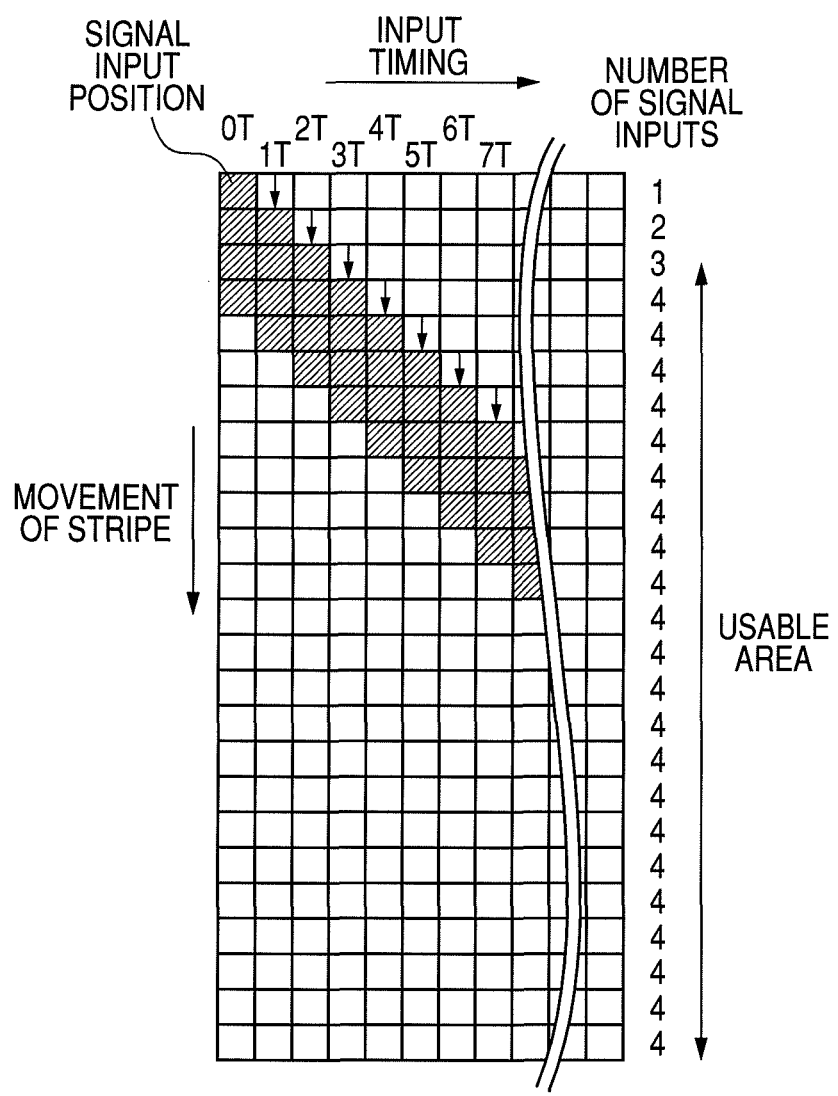
FIG. 17 is a diagram illustrating the time transitions at the time of performing accumulation additions while moving the stripe according to the third embodiment.

The situation will be described with reference to FIG. 16. If each of input signal waveforms is expressed by a small rectangular region by arranging the input signal waveforms into the moving direction as illustrated in FIG. 16, then acoustical wave data 58 in the stripe region 4 can be expressed by N (four in the case of FIG. 16) small rectangles 59 continuing in a longitudinal direction. FIG. 17 illustrates temporal transitions of addition processing by the use of this expression. FIG. 17 illustrates an example of the case of performing signal inputting by using the two-dimensionally arranged elements of N=4 while shifting the stripe position by the longitudinal width of an element. Also in this case, the addition of four times of movements can be performed by the use of the processor 21 similarly to the continuous movement described above.

Figure 18A:
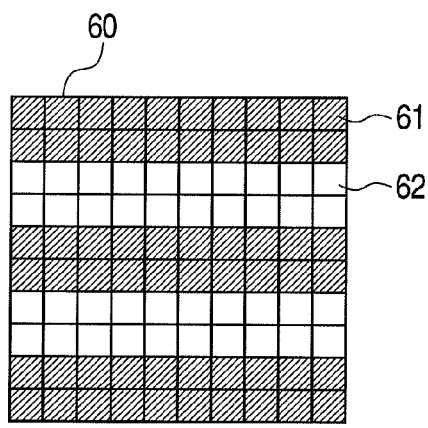
FIGS. 18A and 18B are diagrams illustrating the time transitions at the time of performing the accumulation additions by using an electromechanical conversion element group having gaps according to the third embodiment.
Figure 18B:
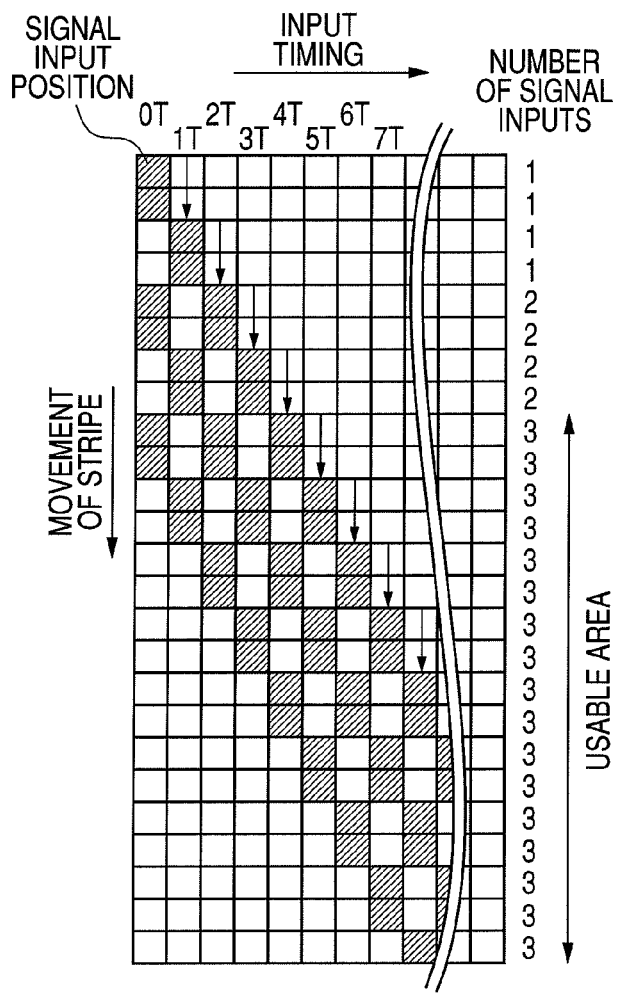

FIG. 18A illustrates an example of the case of using an electromechanical conversion element group 60 having a gap region 62 in an electromechanical conversion element region 61 in the direction (stripe moving direction) perpendicular to the moving direction. Also in this case, three times of accumulation additions can be performed by shifting the stripe position by the longitudinal width of two elements as illustrated in FIG. 18B similarly to the case of the moving direction.

Figure 19:
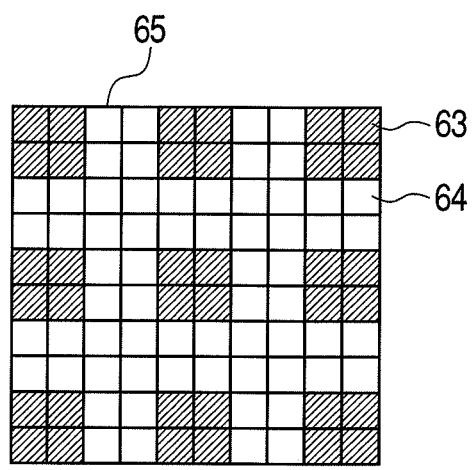
FIG. 19 is a diagram illustrating another example of the electromechanical conversion element group having gaps according to the third embodiment.

FIG. 19 illustrates an example of an electromechanical conversion element group 65 provided with gaps 64 in both of the moving direction and the direction (stripe moving direction) perpendicular to the moving direction of the electromechanical conversion element region 63. Even the electromechanical conversion element group 65 like this can execute positionally dense signal inputting and addition inputting owing to the reason described above.

By performing accumulation additions not only in the moving direction but also in the direction (stripe moving direction) perpendicular to the moving direction by the use of the two-dimensionally arranged electromechanical conversion elements as described above, the number of added signals becomes large, and consequently the SN ratios of the added signals are improved. Since also the illumination unevenness can be smoothed in two dimensions, the image reconstruction having a better quality can be performed.

Since the image reconstruction processing to input signals is frequently linear processing or nearly linear processing, an equivalent advantage can be obtained by adding three-dimensional voxel images after reconstruction in place of adding input signals directly. In this case, the image reconstruction in the stripe region 4 can be performed while inputting the acoustic signals in the stripe region 4, the waste time for waiting the inputting of an adjacent stripe can be lessened.

Fourth Embodiment

Next, a fourth embodiment of the present invention will be described. The fourth embodiment integrates an one-dimensionally arranged transmitting and receiving elements (second electromechanical conversion element group) for ultrasound echo signals and an electromechanical conversion element group (first electromechanical conversion element group) receiving an acoustical wave generated by radiating an electromagnetic wave. The present embodiment is also effective for diagnostic equipment generating an ultrasound echo image and a photoacoustic image at the same time. The other respects of the present embodiment are the same as those of the other embodiments.

Figure 20:
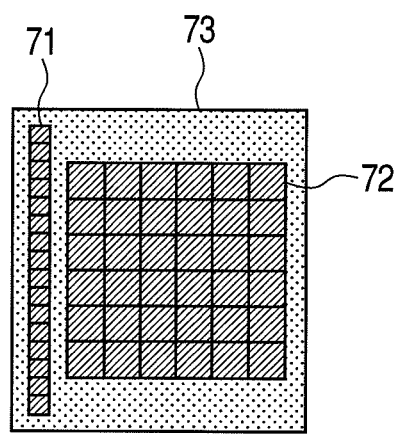
FIG. 20 is a view illustrating an example of arrangement elements configured by combining one-dimensionally arranged transmitting and receiving elements for an ultrasound echo image and two-dimensionally arranged electromechanical conversion elements for a photoacoustic imaging method according to a fourth embodiment.

In the photoacoustic imaging method, it is desirable to use two-dimensionally arranged electromechanical conversion elements for realizing the isotropy of photoacoustic image resolution. It is also desirable against an ultrasound echo image to use a two-dimensionally arranged ultrasound transmitting and receiving elements, but, since the frequency of an ultrasound is relatively high, it is necessary to use many small transmitting and receiving elements, and consequently two-dimensional arrangement causes the problems of the enlargement in size of a signal processing circuit and the enlargement of cost. Accordingly, many practical apparatus input three-dimensional ultrasound echo signals while continuously moving one-dimensionally arranged transmitting and receiving elements. Accordingly, as illustrated in FIG. 20, by forming an integrated structure 73 of one-dimensionally arranged transmitting and receiving elements 71 for ultrasound echo signals and an electromechanical conversion element group 72 arranging electromechanical conversion elements in two dimensions and by continuously moving the integrated structure 73, high quality photoacoustic images and ultrasound echo images can be reconstructed at the same time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2008-159313, filed Jun. 18, 2008, and 2009-029953, filed Feb. 12, 2009, which are hereby incorporated by reference herein in their entirety.

The invention claimed is:

1. An object information acquisition apparatus, comprising:
an electromechanical conversion element group including a plurality of electromechanical conversion elements, each electromechanical conversion element being configured to receive an elastic wave and to convert the received elastic wave into an electric signal, the elastic wave being emitted by a test object in response to the test object being irradiated with an electromagnetic wave;
an actuator configured to mechanically move the electromechanical conversion element group from a first position to a second position; and
an adding circuit configured to add electric signals transmitted from two or more electromechanical conversion elements,
wherein the plurality of electromechanical conversion elements includes a first electromechanical conversion element and a second electromechanical conversion element,
wherein a first electric signal is transmitted from the first electromechanical conversion element to the adding circuit at a first point in time when the first electromechanical conversion element is located at a predetermined position with respect to the test object when the electromechanical conversion element group receives the elastic waves at the first position,
wherein a second electric signal is transmitted from the second electromechanical conversion element to the adding circuit at a second point in time when the second electromechanical conversion element is located at substantially the same predetermined position with respect to the test object when the electromechanical conversion element group receives the elastic waves at the second position, and
wherein the adding circuit adds the first electric signal received from the first electromechanical conversion element to the second electric signal received from the second electromechanical conversion element.

2. The object information acquisition apparatus according to claim 1, further comprising an A/D (analog-to-digital) converter which converts the electric signal transmitted from one of the plurality of electromechanical conversion elements into a digital signal.

3. The object information acquisition apparatus according to claim 1, wherein the electromechanical conversion elements of the electromechanical conversion element group are arranged in a two dimensional grating.

4. The object information acquisition apparatus according to claim 1, wherein the electromechanical conversion element group includes a gap between electromechanical conversion elements, and
wherein a size of the gap is equal to an integral multiple of an arrangement pitch of the electromechanical conversion elements.

5. The object information acquisition apparatus according to claim 4, further comprising an electromagnetic wave source configured to irradiate the test object with the electromagnetic wave,
wherein the electromagnetic wave source is arranged in the gap.

6. The object information acquisition apparatus according to claim 4, wherein the actuator moves the electromechanical conversion element group so that the elastic wave is received after the electromechanical conversion element group has moved from the first position to the second position a distance that is an integral multiple of the size.

7. The object information acquisition apparatus according to claim 1, wherein the electromechanical conversion element group is formed by joining a plurality of electromechanical conversion element groups.

8. The object information acquisition apparatus according to claim 1, wherein electromechanical conversion elements arranged in a direction perpendicular to a moving direction of the electromechanical conversion element group receive elastic waves at the predetermined position with respect to the test object and convert the received elastic waves to electric signals, and
wherein the adding circuit adds the electric signals transmitted from electromechanical conversion elements arranged in the direction perpendicular to the moving direction.

9. The object information acquisition apparatus according to claim 1, further comprising an electromagnetic wave source configured to irradiate the test object with the electromagnetic wave,
wherein the electromagnetic wave source moves, while keeping a relative position with respect to the electromechanical conversion element group.

10. An object information acquisition apparatus comprising:
the electromechanical conversion element group according to claim 1; and
a different electromechanical conversion element group configured to receive a reflected ultrasound radiated to the test object in the test object,
wherein both of the electromechanical conversion element groups are integrally moved.

11. The object information acquisition apparatus according to claim 1, wherein the actuator continuously moves the electromechanical conversion element group parallel to the arrangement direction so that the electromechanical conversion element group receives the elastic wave while continuously moved.

12. The object information acquisition apparatus according to claim 1,
wherein the plurality of the electromechanical conversion elements are arranged in a movement direction in which the electromechanical conversion element group moves, and
wherein the actuator moves the electromechanical conversion element group from the first position to the second position in the movement direction.

13. The object information acquisition apparatus according to claim 1, wherein the actuator is configured to change a position of the electromechanical conversion element group or a position of the electromagnetic wave source with respect to the test object, by mechanically scanning the electromechanical conversion element group or the electromagnetic wave source with respect to the test object.

14. The object information acquisition apparatus according to claim 13, wherein the actuator includes a first direction moving mechanism and a second direction moving mechanism, and
wherein the first direction moving mechanism moves the electromechanical conversion element group or the electromagnetic wave source with respect to the test object in a first direction, and the second direction moving mechanism moves the electromechanical conversion element group or the electromagnetic wave source with respect to the test object in a second direction perpendicular to the first direction.

15. An object information acquisition apparatus, comprising:
an electromechanical conversion element group including a plurality of electromechanical conversion elements, each electromechanical conversion element being configured to receive an elastic wave and to convert the received elastic wave into an electric signal, the elastic wave being emitted from a test object in response to the test object being irradiated with an electromagnetic wave;
an actuator configured to mechanically move the electromechanical conversion element group from a first position to a second position; and
an adding circuit configured to add electric signals transmitted from two or more electromechanical conversion elements,
wherein the plurality of electromechanical conversion elements includes a first electromechanical conversion element and a second electromechanical conversion element,
wherein a first electric signal is transmitted from the first electromechanical conversion element to the adding circuit at a first point in time when a predetermined point in the test object is irradiated with the electromagnetic wave and the electromechanical conversion element group receives the elastic waves at the first position,
wherein a second electric signal is transmitted from the second electromechanical conversion element to the adding circuit at a second point in time when the same predetermined point in the test object is again irradiated with the electromagnetic wave and the electromechanical conversion element group receives the elastic waves at the second position, and
wherein the adding circuit adds the first electric signal received from the first electromechanical conversion element to the second electric signal received from the second electromechanical conversion element.

* * * * *